United States Patent [19]

Singhal

[11] Patent Number: 4,683,316
[45] Date of Patent: Jul. 28, 1987

[54] METHOD OF PREPARATION OF DITHIOCARBAMATE COMPLEXES OF MOLYBDENUM (VI)

[75] Inventor: Gopal H. Singhal, Houston, Tex.

[73] Assignee: Exxon Research and Engineering Company, Florham Park, N.J.

[21] Appl. No.: 815,604

[22] Filed: Jan. 2, 1986

[51] Int. Cl.[4] .............................................. C07F 11/00
[52] U.S. Cl. ..................................................... 556/38
[58] Field of Search ......................................... 556/38

[56] References Cited

U.S. PATENT DOCUMENTS

| | | | |
|---|---|---|---|
| 3,356,702 | 12/1967 | Farmer et al. | 556/38 |
| 3,419,589 | 12/1968 | Larsen et al. | 556/38 |
| 4,098,705 | 7/1978 | Sakurai et al. | 556/38 X |
| 4,588,829 | 5/1986 | Pan et al. | 556/38 |

FOREIGN PATENT DOCUMENTS

| | | | |
|---|---|---|---|
| 133309 | 12/1974 | Japan | 556/38 |
| 80825 | 7/1976 | Japan | 556/38 |

OTHER PUBLICATIONS

Moore and Larsen, *Inorganic Chemistry*, vol. 6, No. 5, May 1967, pp. 998–1003.
R. N. Jowitt and P. C. M. Mitchell, J. Chem. Soc. (A), 1702–1708 (1970).
Pandeya and Kaul, Synth. React. Inorga. Met.-Org. Chem., 12(3), 259–268 (1982).

*Primary Examiner*—Helen M. S. Sneed
*Attorney, Agent, or Firm*—Wayne Hoover

[57] ABSTRACT

An improved process for preparing dihydrocarbyl substituted dithiocarbamates of molybdenum (VI) wherein an alkali metal ammonium or substituted ammonium salt of a dihydrocarbyl substituted dithiocarbamate is reacted with an alkali metal molybdate in the presence of an organic acid. The process is carried out in an inert atmosphere and within a relatively narrow range of temperatures. The dihydrocarbyl substituted dithiocarbamate of molybdenum (VI) may be recrystallized after preparation to increase its purity. The dihydrocarbyl substituted dithiocarbamate of molybdenum (VI) is produced at a temperature within the range from about $-10°$ C. to about $+25°$ C. at a pH during neutralization within the range from about 5.0 to about 8.0.

13 Claims, 3 Drawing Figures

METHOD OF PREPARATION OF DITHIOCARBAMATE COMPLEXES OF MOLYBDENUM (VI)

BACKGROUND OF THE INVENTION

This invention relates to a method for preparing metal organic compounds. More particularly, this invention relates to a method of preparing hydrocarbyl substituted dithiocarbamates of molybdenum. Still more particularly, this invention relates to a method of preparing hydrocarbyl substituted dithiocarbamates of molybdenum containing molybdenum in a VI+ oxidation state.

Processes for preparing hydrocarbyl substituted dithiocarbamates or molybdenum (VI) have been proposed heretofore. In such processes, a solution of an alkali metal hydrocarbyl substituted dithiocarbamate and an alkali metal molybdate is neutralized with an inorganic acid such as nitric acid, hydrochloric acid, etc., followed by extraction and oxidation with a strong oxidizing agent such as t-butylhydroperoxide. These processes have not, however, been effective for the production of dithiocarbamates of molybdenum (VI) with hydrocarbyl substituted groups containing more than about four carbon atoms. Moreover, the extraction and oxidation steps required by the prior art processes complicate the production of such hydrocarbyl substituted dithiocarbamates. Further, when the hydrocarbyl groups are branched rather than straight chained, disubstituted dithiocarbamates of molybdenum VI could not be prepared and unidentified tars which could not be purified resulted. Still further, in the preparation of dihydrocarbyl substituted dithiocarbamates with these prior art processes, a 50% excess of sodium molybdate has been recommended. These methods, then, are wasteful and do not fully utilize the metal. Finally, these methods of producing such hydrocarbyl substituted dithiocarbamates are indirect and not well suited for large scale preparations.

Recently, it has been learned that certain dihydrocarbyl substituted dithiocarbamates of various metals are particularly effective catalyst precursors in certain hydroconversion processes. This discovery is the subject of co-pending U.S. patent application Ser. No. 608,308 which was filed on May 8, 1984. More recently, it has been discovered that dihydrocarbyl substituted dithiocarbamates of molybdenum (VI) are particularly effective as catalyst precursors in certain of these hydroconversion processes. In light of these discoveries, the need for a process for preparing dihydrocarbyl substituted dithiocarbamates having about four or more carbon atoms in the hydrocarbyl substitution and the need for an improved process for making such dithiocarbamates wherein the hydrocarbyl substitution contains from about 1 to 3 carbon atoms is, then, believed to be readily apparent.

SUMMARY OF THE INVENTION

It has now been discovered that the foregoing and other disadvantages and deficiencies of the prior art processes for the production of dihydrocarbyl substituted dithiocarbamates of molybdenum (V) can be avoided with the method of the present invention and an improved process for preparing such compounds when each of the hydrocarbyl substitutions contain from 1 to 3 carbon atoms and a process for preparing such compounds wherein the hydrocarbyl substituents contain about 4 or more carbon atoms which may be branched, straight chained, cyclic, aromatic or mixtures thereof, provided thereby. It is, therefore, an object of this invention to provide an improved process for the preparation of dihydrocarbyl substituted dithiocarbamates of molybdenum (VI). It is another object of this invention to provide a process for the preparation of dihydrocarbyl substituted dithiocarbamates of molybdenum (VI) wherein the dihydrocarbyl substituents contain about 4 or more carbon atoms. It is still another object of this invention to provide such a process wherein the amount of impurities produced is reduced. It is still a further object of this invention to provide such a process wherein the yield of dihydrocarbyl substituted dithiocarbamates of molydenum (VI) is increased and the metal is more effectively utilized. It is yet another object of this invention to provide such a process wherein the purity of the dihydrocarbyl substituted dithiocarbamate of molybdenum (VI) is improved. The foregoing and other objects and advantages will become apparent from the description set forth hereinafter and from the drawings appended thereto.

In accordance with the present invention, the foregoing and other objects and advantages are accomplished by combining an alkali metal salt, an ammonium salt or a substituted ammonium salt of a dihydrocarbyl substituted dithiocarbamate and an alkali metal molybdate (molybdenum VI) in a suitable solvent in the presence of an organic acid. Following the reaction or neutralization, the resulting product may be recrystallized to yield the dihydrocarbyl substituted dithiocarbamate of molybdenum (VI) in higher yields and in higher purity. The alkali metal salt of the dihydrocarbyl substituted dithiocarbamate used as a reactant may be produced in accordance with known techniques by first combining a dihydrocarbyl substituted amine and carbon disulfide and thereafter adding an alkali metal hydroxide. In the method of the present invention, it is important that the pH during the acidification of the dihydrocarbyl substituted dithiocarbamate be controlled within the range from about 5 to about 8. It is also important that oxygen be excluded during this step.

DETAILED DESCRIPTION OF THE INVENTION

Figure 1:
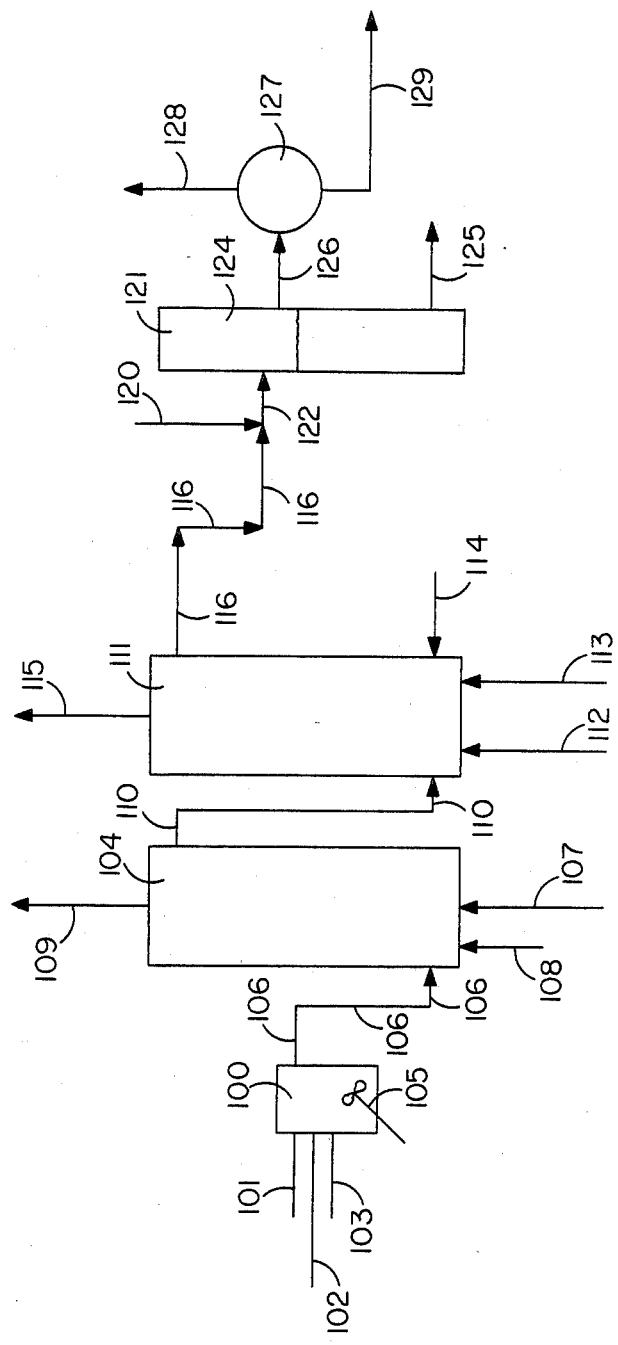
FIG. 1 is a schematic flow diagram of a process within the scope of the present invention.

As indicated, supra, the present invention relates to an improved process for preparing dihydrocarbyl substituted dithiocarbamates of molybdenum (VI) and to a process for preparing dihydrocarbyl substituted dithiocarbamates of molybdenum (VI) wherein 1 or more of the hydrocarbyl substituents contains about 4 or more carbon atoms. In general, the preparation may be completed in a single step by combining an alkali metal salt, an ammonium salt or a substituted ammonium salt of a dihydrocarbyl substituted dithiocarbamate with an alkali metal molybdate comprising molybdenum (VI) in a suitable solvent with an organic acid. After the reaction has been completed, the dihydrocarbyl substituted dithiocarbamate of molybdenum (VI) may be separated directly from the reaction media and recovered in relatively high yield and purity. The separation may be accomplished using any of the techniques known in the prior art to be suitable for such separation. For example, when the dihydrocarbyl substituted dithiocarbamate of molybdenum (VI) is insoluble in the reaction media, filtration, centrifugation and the like may be used. When the dihydrocarbyl substituted dithiocarbamate of molybdenum (VI) is soluble in the reaction medium, on the other hand, the reaction media may be distilled off to leave a solid product or an anti-solvent may be added so as to preciptate the dihydrocarbyl substituted dithiocarbamate of molybdenum (VI) and the same then separated via filtration, centrifugation and the like. Frequently, and particularly where the dihydrocarbyl substituted dithiocarbamate of molybdenum (VI) is soluble in the reaction medium, the product will be recovered in relatively high purity and no further purification will be necessary. When increased purity is, however, desired, such increased purity may be achieved by dissolving the dihydrocarbyl substituted dithiocarbamate of molybdenum (VI) in a suitable solvent and then recrystallizing the same.

In general, the alkali metal salt, an ammonium salt or substituted ammonium salt of a dihydrocarbyl substituted dithiocarbamate useful in the process of the present invention will have the following general formula:

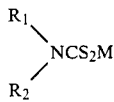

Wherein:

$R_1$ and $R_2$ may be the same or different hydrocarbon radicals selected from the group consisting of $C_1$–$C_{18}$ straight and branched chain aliphatic radicals; $C_5$–$C_8$ cycloalkyl radicals; alkyl substituted cycloalkyl radicals having from 1 to 3 carbon atoms in the alkyl group and from 5 to 7 carbon atoms in the cycloalkyl group; aryl and alkylaryl radicals having from 1 to 4 carbon atoms in the alkyl portion thereof and 6 carbon atoms in the aryl portion thereof and $R_1$ and $R_2$ may also be a single cyclo or cycloalkyl radicals having from about 5 to about 10 carbon atoms and;

M is a cation selected from the group consisting of lithium, sodium, potassium, rubidium, cesium, ammonium and substituted ammonium groups wherein one or more of the hydrogen atoms of an ammonium ion are replaced with a hydrocarbon radical, as defined above.

The alkali metal molybdate useful in the present invention will have the general formula:

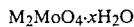

Wherein:

M is an alkali metal atom selected from the group of metals consisting of lithium, sodium, potassium, rubidium and cesium; and x is an integer having a value of 1, 2, 3, 4 or 5.

In general, the alkali metal salt of the dihydrocarbyl substituted dithiocarbamate will be combined with the alkali metal molybdate in a suitable solvent which in turn will serve as a reaction media. Selection of a suitable solvent is, of course, well within the ordinary skill of the art. Suitable solvents may be both organic and inorganic and include, but are not limited to, water, alkanes such as hexane and heptane, aromatics such as benzene and toluene, halogenated hydrocarbons such as chloroform, methylene chloride, and the like. Mixed solvents such as water-toluene, water-chloroform, water-benzene and the like may also be used. During the neutralization reaction, sufficient organic acid will be present to maintain a pH within the range from about 5 to about 8. In general, any organic acid may be used, but acids containing a single carboxylic acid group are most effective and are, therefore, preferred. Suitable organic acids include monocarboxylic acids such as formic acid, acetic acid, propionic acid, benzoic acid and alkyl substituted benzoic acids such as methylbenzoic acid, ethylbenzoic acid and the like. Generally, the reaction media will be selected such that the acid employed will be soluble therein.

As indicated in co-pending application Ser. No. 771,865 which was filed Sept. 3, 1985, certain salts of dithiocarbamate are apparently unstable in the presence of air of oxygen. As a result, it is important to the process of the present invention that the reaction between the alkali metal salt of dithiocarbamate and the alkali metal molybdate be carried out in an inert atmosphere and particularly in the absence of an oxidizing agent such as air, oxygen or the like.

In general, acidification of the alkali metal salt, ammonium salt or substituted ammonium salt of dithiocarbamate and alkali metal molybdate will be accomplished at a temperature within the range from about −10° to about 25° C. and at a pressure within the range from about ambient pressure to about 100 psig. In general, the acidification will be accomplished by contacting the reactants at reaction conditions for a nominal holding time within the range from about 10 to about 500 minutes. As indicated previously, the acidification will be accomplished in an inert atmosphere and in the absence of any oxidizing agents such as oxygen, air or the like. By accomplishing the acidification within a relatively narrow temperature range and in the absence of oxidizing agents, the production of tars which has occurred in similar processes proposed heretofore is avoided. Moreover, and as indicated more fully hereinafter, controlling the temperature within an even narrower range than is broadly contemplated in the present invention will avoid or at least significantly reduce the yield of dihydrocarbyl substituted dithiocarbamate of molybdenum dimer and tars thereby yielding a product of much higher purity than has heretofore been obtained.

As indicated, supra, the dihydrocarbyl substituted dithiocarbamate of molybdenum (VI) can be recovered in high purity simply by evaporating off the reaction media or by adding an anti-solvent and then filtering the same from the reaction media. A particularly preferred method of recovery is to effectively extract the dihydrocarbyl substituted dithiocarbamate of molybdenum (VI) from the reaction media using a suitable solvent and thereafter washing, drying and filtering the extract. In a most preferred embodiment of the present invention, the dihydrocarbyl substituted dithiocarbamate of molybdenum (VI) will then be recrystallized in a suitable medium. Any suitable solvent known in the prior art may be used to extract the dihydrocarbyl substituted dithiocarbamate of molybdenum (VI) from the reaction medium. Such solvents include lower boiling aromatics and substituted aromatics such as benzene and toluene as well as halogenated hydrocarbons such as chloroform, dichloromethane and trichloromethane. In order to separate the dihydrocarbyl substituted dithiocarbamate of molybdenum (VI) in this manner, the suitable solvent will be combined with the reaction media, thoroughly mixed and then separated from the reaction media via a suitable technique such as decanting. The extract may then be washed with a suitable media such as water, dried and filtered. The filtrate may then be concentrated to dryness under reduced pressure and the residue recrystallized in a suitable medium. Suitable media for recrystallization include benzene-hepatane, toluene-petroleum ether and toluene-heptane.

PREFERRED EMBODIMENT

In a preferred embodiment of the present invention, an alkali metal salt of dithiocarbamate will be prepared in a separate step under an inert atmosphere prior to reacting the same with an alkali metal molybdate in the presence of an organic acid. The alkali metal salt will then be maintained in an inert atmosphere until its subsequent reaction with the alkali metal molybdate. In the preferred embodiment, the alkali metal salt of dithiocarbamate will be prepared by reacting an alkali metal hydroxide, a dihydrocarbyl substituted amine and carbon disulfide at a temperature within the range from about $-5°$ to about $30°$ C. Nominal contacting or holding times within the range from about 10 to about 240 minutes will be used to insure complete conversion of the reactant or reactants. In general, equal molar or stoichiometric amounts of all reactants will be combined in the preparation of said alkali metal salt of dithiocarbamate, however, a slight excess of carbon disulfide will increase the reaction rate. In the preferred embodiment, the pH of the reaction media during the preparation of the alkali metal salt of dithiocarbamate will be controlled within the range from about 7.5 to about 12.

In a most preferred embodiment of the present invention and in the preparation of the alkali metal salt of dithiocarbamate, stoichiometric quantities of a dialkylamine and carbon disulfide will be combined in water and thoroughly mixed. After the mixing is completed, a stoichiometric quantity of an alkali metal hydroxide, most preferably sodium hydroxide, will be added to the thoroughly mixed mixture and reacted with the dialkylamine and the carbon disulfide at a temperature within the range from about $-5°$ to about $30°$ C. The reactants will be maintained within this temperature range for a nominal holding time within the period from about 10 minutes to about 240 minutes. In the preferred embodiment, the dialkylamine may comprise the same or different alkyl groups, each having from about 1 to about 18 carbon atoms. The reaction of the dialkylamine, carbon disulfide and the alkali metal hydroxide will be accomplished in an inert atmosphere and most preferably in the presence of nitrogen. The sodium salt of the dialkyl substituted dithiocarbamate thus produced will then be combined with a stoichiometric quantity of an alkali metal molybdate, most preferably sodium molybdate, and acidified with a solution of glacial acetic acid in water. The acidification will preferably be accomplished at a temperature within the range from about $-5°$ to about $5°$ C., at a pH within the range from about 6.0 to about 7.5, and in an inert atmosphere, most preferably in the presence of nitrogen. The nominal holding time during acidification will be for a period of time within the range from about 10 minutes to about 500 minutes.

A continuous process within the scope of the present invention and one in which a preferred embodiment thereof may be carried out is illustrated in the attached FIG. 1 and it is believed that the invention will be better understood by reference to this FIG. 1. Referring then to this figure, a solution of a dihydrocarbyl substituted amine, preferably an aqueous solution thereof, will be introduced into mixing vessel 100 through line 101 and combined with carbon disulfide introduced through line 102 and any additional water that may be required introduced through line 103. In general, the weight ratio of reactants to solvent, preferably water, in the first reactor 104 will be within the range from about 1:2 to about 1:100, on a weight basis. Sufficient water will, then, be added through line 103 to provide a ratio within this range giving due consideration to the amount of solvent, preferably water, that may be subsequently added with the hydroxide. In mixing vessel 100, the dihydrocarbyl substituted amine and the carbon disulfide will be thoroughly mixed with the solvent, preferably water. The mixing may be facilitated through the use of suitable means such as agitator 105.

The mixture is withdrawn from mixing vessel 100 through lines 106—106 and passed to first reactor 104. A solution of an alkali metal, ammonium or substituted ammonium hydroxide, most preferably an aqueous solution of sodium hydroxide, will be introduced into reactor 104 through line 107. An inert gas, preferably nitrogen, will be introduced into reactor 104 through line 108. In general, reactor 104 will be operated at a temperature within the range from about $-5°$ to about $30°$ C., In reactor 104, the dihydrocarbyl substituted amine, the carbon disulfide and the hydroxide will react to produce an alkali metal, ammonium or substituted ammonium salt of dithiocarbamate. The reaction is completed in an inert atmosphere due to the introduction of an inert gas through line 108, which inert gas will be withdrawn through line 109 and may be recycled through line 108, though not illustrated. In general, any relative ratio of reactants may be employed, but stoichiometric amounts of reactants will preferably be used so as to avoid the presence of unreacted reagents in the product and to improve the utilization of reactants.

The effluent from reactor 104 which will consist primarily of a solution, preferably an aqueous solution, of an alkali metal, ammonium or a substituted ammonium salt of a dihydrocarbyl substituted dithiocarbamate will be withdrawn through lines 110—110 and passed to a second reactor 111. A solution of a stoichiometric amount of an alkali metal molybdate, most preferably an aqueous solution of sodium molybdate, will be introduced into reactor 111 through line 112. A sufficient amount of organic acid, preferably an aqueous solution thereof, will be introduced into the reactor 111 through line 113 to maintain the pH of the effluent from the reactor within the range from about 5.0 to about 8.0. Reactor 111 will be operated generally at a temperature within the range from $-10°$ C. to about $+25°$ C. and preferably at a temperature within the range from about $-5°$ C. to about $+5°$ C. In reactor 111, the salt of the dihydrocarbyl substituted dithiocarbamate and the alkali metal molybdate will be acidified to produce the corresponding dihydrocarbyl substituted dithiocarbamate of molybdenum (VI). To ensure that the reaction carried out in reactor 111 is completed in an inert atmosphere, an inert gas will be introduced into reactor 111 through line 114 and withdrawn through line 115. One advantage of this method is that in reactor 111, at no time will there be an excess of acid or salt of a dihydrocarbyl substituted-dithiocarbamate. In cases in which dithiocarbamate product is initially formed as a viscous material, and in a most preferred embodiment, an organic solvent such as toluene or chloroform will be introduced into the reactor through line 130. Alternatively, and especially when the product is not particularly viscous, the organic solvent may be added to the effluent from reactor 111 which is withdrawn through lines 116—116. In this case, the organic solvent for the dihydrocarbyl substituted dithiocarbamate of molybdenum (VI) will be introduced through line 120.

In any case, the effluent and the added organic solvent is passed to suitable separating means 121 through line 122. In the embodiment illustrated, a settling vessel has been illustrated as a suitable separating means. When such a means is employed, the settler must be properly sized to permit separation of the hydrocarbon phase and the water phase, when water is used as the reaction medium in reactor 111. The water will, of course, settle to the lower section of the separating vessel 121 when the added organic solvents have a lower density than water and the water may be withdrawn through line 125. The hydrocarbon phase, on the other hand, which will comprise the dihydrocarbyl substituted dithiocarbamate of molybdenum (VI) will float to the upper portion of vessel 124 and may be withdrawn through line 126. It will, of course, be appreciated that the aqueous phase withdrawn through line 125 could be recycled through line 103 to mixing vessel 100. It will also be appreciated that when heavier solvents such as chloroform are used, the water phase would float and be withdrawn through line 126 while the hydrocarbon phase would be withdrawn through line 125. In any case, the hydrocarbon phase, which is withdrawn through line 126 in the embodiment illustrated, is then passed to a suitable separating means 127 to recover the dithiocarbmate product. In the embodiment illustrated, the suitable separating means is simply a flash drum wherein the solvent is flashed overhead and withdrawn through line 128 and the dihydrocarbyl substituted dithiocarbamate of moybdenum (VI) is withdrawn through line 129. As indicated, supra, and while not illustrated, the product withdrawn through 129 could be recrystallized in a suitalbe media to thereby improve the purity thereof, if desired.

Having thus broadly described the present invention and a preferred embodiment thereof, it is believed that the same will become even more apparent by reference to the following examples. It will be appreciated, however, that the examples are presented solely for purposes of illustration and should not be construed as limiting the invention. All of the following experiments were carried out on ice baths at a temperature of approximately 0° C.

EXAMPLE 1

In this example, Dioxobis(N,N-dibutyldithiocarbamato)Mo(VI) was prepared as follows: To a stirred solution of 12.1 g of sodium dibutyldithiocarbamate in 600 ml of water on an ice bath was added a solution of 6.0 g sodium molybdate dihydrate in 200 ml of water. To the resulting solution was added with stirring a solution of 12 g of glacial acetic acid in 250 ml of water.

The mixture was extracted with 250 ml of methylene chloride. The bottom layer was separated, washed with water, dried over $MgSO_4$ and filtered. The filtrate was concentrated to dryness under reduced pressure and the residue was recrystallized from toluene-heptane. The yield of Dioxobis(N,N-dibutyldithiocarbamato)-Mo(VI), a yellow crystalline material, was 10.3 g (74% conversion). The identity of the material was established by IR and NMR analysis.

EXAMPLE 2

The preparation summarized in Example 1 was repeated with the exception that the mixture of water solution obtained upon addition of sodium molybdate to sodium dibutyldithiocarbamate was added to the stirred acetic acid solution rather than the acid being added to the water solution. A yellow precipitate with a tendency to gum formation was obtained after this addition. Extraction, separation, etc., as in Example 1 then gave orange crystals in 10 g yield.

EXAMPLE 3

The preparation summarized in Example 1 was repeated with the exception that mother liquor from Example 2 was used for the preparation. Dioxobis(N,N-dibutyldithiocarbamato)Mo(VI) was obtained in a 60% yield.

EXAMPLE 4

In this example, Dioxobis(N,N-dipropyldithiocarbamato)Mo(VI) was prepared as follows: To an ice and stirred solution of sodium dipropyldithiocarbamate prepared from 0.1 mole of dipropylamine, 0.1 mole of $CS_2$ and 0.1 mole of NaOH, a solution of 12.5 g (0.05 mole) of sodium molybdate, dihydrate was added and the solution was acidified with dilute acetic acid. The usual workup gave orange-yellow crystalline material in 75% yield.

EXAMPLE 5

In this example, Dioxobis(N,N-diisobutyldithiocarbamato)Mo(VI) was prepared by the method summarized in Example 1 with the exception that diisobutylamine was used in place of dibutylamine and the amounts of material except water was doubled. The yield of the desired product as a yellow crystalline material was 18.6 g (69% conversion).

EXAMPLE 6

In this example, Dioxobis(N,N-dibutyldithiocarbamato)Mo(VI) was prepared as follows: An ice cold solution of a mixture of 0.1 mole of sodium dibutyldithiocarbamate and 0.05 mole of sodium molybdate dihydrate in 400 ml of water was added with stirring to an ice cold solution of 0.21 mole of propionic acid in 500 ml of water. The resulting mixture was extracted with 400 ml of $CH_2Cl_2$ in three portions. The $CH_2Cl_2$ solution was washed with water, dried over $MgSO_4$, filtered and concentrated to dryness under reduced pressure. The residue on crystallization from toluene-heptane gave the product as an orange-yellow crystalline material, 18.1 g (67% conversion).

EXAMPLE 7

In this example, Dioxobis(N,N-dibutyldithiocarbamato)Mo(VI) was prepared as follows: To a stirred solution of 24.3 g of potassium dibutyldithiocarbamate in 1700 ml of water-ice mixture was added a solution of 12.3 g of sodium molybdate dihydrate in 500 ml of water. To the clear solution at 0°-5° C. under $N_2$ purge 400 ml of toluene were added and then was added through a dropping funnel a solution of 12.7 ml of acetic acid in 400 ml of ice water. To the orange-yellow mixture, 500 ml of toluene was added and stirred for 10 min. The toluene layer was separated, water layer extracted with toluene (2×100 ml). The combined toluene solutions were washed with water, dried over MgSO$_4$, filtered and concentrated to a small volume. Addition of petroleum ether and cooling gave 18.8 g (70% conversion) of yellow solid. A sample was recrystallized from toluene-petroleum ether. The product had a melting point of 71°–72° C. and showed strong Mo(VI) characteristic peaks at 880 cm$^{-1}$ and 920 cm$^{-1}$. The analysis obtained is compared with theoretical analysis below:

Analysis Obtained: C, 40.27; H, 6.62; N, 5.19; Mo, 18.2

Theoretical Analysis: C, 40.30; H, 6.72; N, 5.22; Mo, 17.91.

Figure 2:
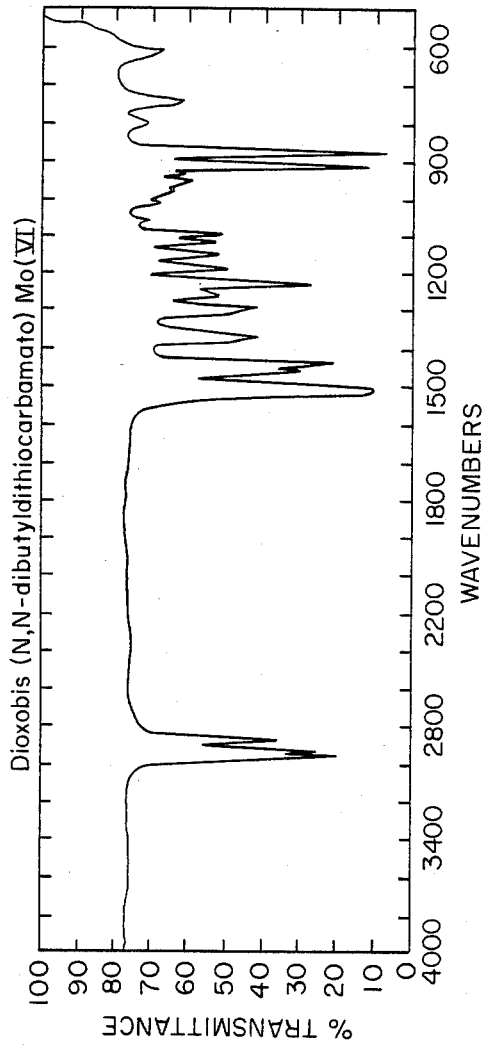
FIG. 2 is an infrared spectrum of a Dioxobis(N,N-dibutyldithiocarbamato)Mo(VI) prepared by the method of this invention.

An infrared spectrum of the product obtained in this Example is attached as FIG. 2. The peaks at about 880 and about 910 are characteristic of molybdenum in VI$^-$ oxidation state.

EXAMPLE 8

In this example, Dioxobis(N,N-diethyldithiocarbamato)Mo(VI) was prepared as follows: To a stirred solution of 22.5 g of sodium diethyldithiocarbamate trihydrate in 1500 ml of deaerated ice water mixture with N$_2$ bubbling were added sequentially a solution of 13.2 ml of glacial acetic acid in 500 ml of cold deaerated water and a solution of 14.5 g of Na$_2$MoO$_4$.2H$_2$O in water. A bright yellow solid precipitated out almost immediately. The stirring was continued for 30 minutes and then the solid was collected by filtration washed well with water, once with ethanol, petroleum ether and dried. The yield of the product was 18.9 g (89% conversion). An infrared spectrum of the product confirmed its structure.

EXAMPLE 9

In this example, the procedure summarized in Example 8 was repeated with the exception that 14 g of sodium molybdate dihydrate was taken and 15.1 g of propionic acid was used for neutralization. The yield of the product was 16.6 g (79% conversion). A sample was recrystallized from methylene chloride, petroleum ether and an elemental analysis was carried out. The analysis obtained is compared with the theoretical analysis below:

Analysis obtained: C, 28.30; H, 4.72; N, 6.60; Mo, 22.64;

Theoretical Analysis: C, 28.09; H, 4.71; N, 6.55; Mo, 22.50.

EXAMPLE 10

In this example, Dioxobis(N,N-pentamethylenedithiocarbamato)Mo(VI) was prepared by repeating the procedure summarized in Example 7 using 18.3 g of sodium piperidinyl-dithiocarbamate, 12.9 g of sodium molybdate dihydrate and 12.5 g of acetic acid. The yield of the product which was obtained as a dull yellow solid was 19.2 g (85% conversion). A sample was recrystallized from methylene chloride-petroleum ether to give a dull yellow crystalline solid and an elemental analysis was then completed on this sample. The analysis obtained is compared with the theoretical analysis below:

Analysis Obtained: C, 32.14; H, 4.46; N, 6.25; Mo, 21.43;

Theoretical Analysis: C, 32.28; H, 4.49; N, 6.13; Mo, 22.0.

An infrared spectrum was consistent with the structure.

EXAMPLE 11

In this example, Dioxobis(dicyclohexyldithiocarbamato)Mo(VI) was prepared as follows: To a stirred solution of 7.2 g of sodium molybdate dihydrate in 1500 ml of deaerated ice water mixture were added 14.8 g of potassium dicyclhexyldithiocarbamate and 500 ml of chloroform. To the stirred mixture with N$_2$ bubbling through the mixture was added a solution of 7.2 ml of glacial acetic acid in 400 ml of deaerated cold water.

The mixture was stirred for 90 minutes, chloroform layer was separated, washed with water, dried over MgSO$_4$ and filtered. The filtrate was concentrated to dryness under reduced pressure and the residue was recrystallized from methylene chloride-petroleum ether.

The yield of orange-yellow crystalline product was 7.7 g. An infrared spectrum of the product was consistent with the structure. The analysis obtained is compared with the theoretical analysis below:

Analysis Obtained: C, 48.75; H, 6.88; N, 4.38; Mo, 14.9;

Theoretical Analysis: C, 48.69; H, 6.71; N, 4.33; Mo, 15.0.

EXAMPLE 12

In this example, Dioxobis(dioctyldithiocarbamato)M0(VI) was prepared as follows: To a stirred solution of 24.5 g (0.1 mole) of Na$_2$MoO$_4$.2H$_2$O in 1800 ml of deaerated water under N$_2$ were added crude potassium dioctyldithiocarbamate prepared from 48.2 g (0.2 mole) of dioctylamine and 600 ml of chloroform. To the stirred mixture under N$_2$ was added through a dropping funnel a solution of 25 g of glacial acetic acid in 600 ml of deaerated cold water. The color of the mixture changed from yellow to red-orange. After allowing to stir for 90 minutes, the chloroform layer was separated, washed with cold water, dried over MgSO$_4$ and filtered. The filtrate was concentrated to dryness on a Rotovap and then subjected to high vacuum at 60° C. for 2 hours.

The yield of the product as a thick oil was 66.1 g (86% conversion). An infrared spectrum of the product showed strong peaks at 880 cm$^{-1}$ and 910 cm$^{-1}$ (Mo VI). In addition, a smaller peak at 930 cm$^{-1}$ indicated the presence as a small amount of (MoV).

EXAMPLE 13

In order to avoid an excess of the acid or the liquid in preparing dialkyl-substituted dithiocarbamates of Mo(VI), the method of addition may be further varied. Particularly, both the solution of the ligand in a solvent (preferably deaerated cold water) and the solution of acid (preferably deaerated cold water) can be added to a solution of sodium molybdate (preferably deaerated ice-water). With this variation, the products are obtained in good yields and relatively pure condition. This example illustrates this variation.

In this example, Dioxobis(dibutyldithiocarbamato)-Mo(VI) was prepared as follows: To a stirred solution of 12.1 g (0.05 mole) of Na$_2$Mo$_4$.2H$_2$O in 1500 ml of deaerated water on an ice salt bath were added concurrently solutions of 24.3 g of potassium dibutyldithiocarbamate in 500 ml of cold deaerated water and a solution of 12.6 ml of glacial acetic in 500 ml of deaerated cold water while bubbling $N_2$ through the mixture. To the mixture 500 ml of toluene was added and the stirring was continued for 30 minutes. The mixture was allowed to settle and the toluene layer separated washed with water (2×200 ml) of water, dried over $Na_2SO_4$ and filtered. The filtrate was concentrated to one-half, diluted with petroleum ether and cooled in an ice bath.

The resulting yellow crystalline solid was collected and dried. The yield was 18.8 g (70% conversion). The melting point of the product was 70.5°–72° C. An infrared spectrum confirmed the structure of the product.

EXAMPLE 14

In this example, Dioxobis(dibutyldithiocarbamato)Mo(VI) was prepared using the method of addition summarized in Example 13 as follows: To a stirred solution of 25 g $Na_2Mo_4.2H_2O$ in 1800 ml deaerated ice water, 600 ml of toluene was added. To the mixture under $N_2$ were added through dropping funnel and concurrently solutions of 48.6 g (0.2 ml of potassium dibutyldithiocarbamate in 400 ml of deaerated ice water and a solution of 25 g of glacial acetic acid in 500 ml of deaerated ice water. The mixture was stirred for 1 hour with $N_2$ bubbling on the ice bath and then allowed to settle. The bottom layer was carefully siphoned off. To the solution, 1000 ml ice cold water was added and stirred for 10 minutes, allowed to settle and water wash was again removed. To the solution, petroleum ether was added and the mixture stirred for a few minutes. The resulting solid was collected by filtration, washed with petroleum ether, dried and recrystallized from toluene-petroleum ether.

The yield of the product as a yellow crystalline solid was 35.2 g (66% conversion). The product has a melting point of 71°–72°. An infrared of the product was consistent with the structure.

EXAMPLE 15

In this example, Dioxobis(diisopropyldithiocarbamato)Mo(VI) was prepared using the method of addition summarized in Example 13 as follows: To a mechanically stirred solution of 2.5 g of $Na_2MoO_4.2H_2O$ (0.05 mole) in 1700 ml of deaerated ice water mixture were added under $N_2$ concurrently solutions of 21.52 g (0.1 mole) of potassium diisopropyldithiocarbamate and 12.5 g of glacial acetic acid in 420 ml each of cold deaerated water.

As the solutions were added, a yellow precipitate separated out. The mixture was stirred for 90 minutes after the addition of the solutions was complete. The yellow solid was collected in filtration, washed with water and dried to give 14.4 g (60% conversion) of the product as a yellow solid with greenish tint.

Figure 3:
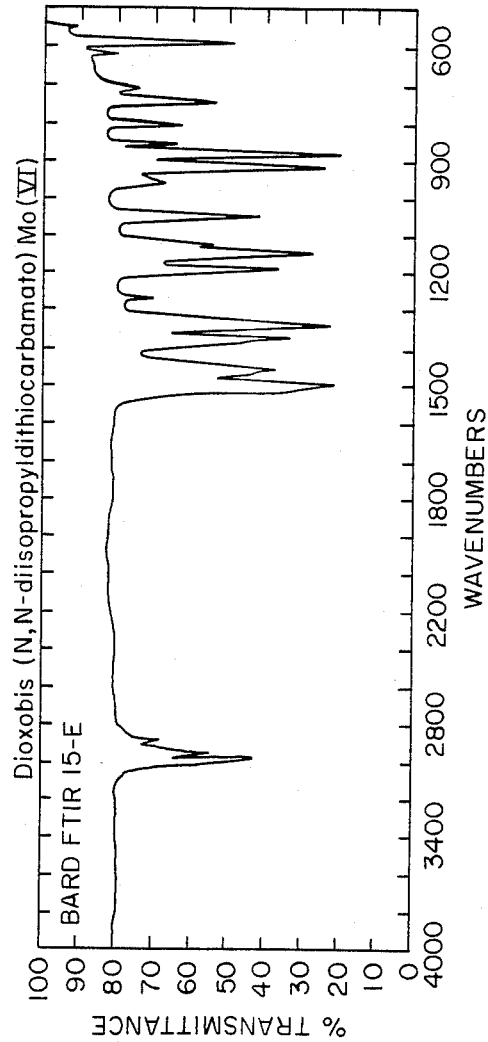
FIG. 3 is an infrared spectrum of a Dioxobis(N,N-diisopropyldithiocarbamato)Mo(VI) prepared by the method of this invention.

A sample was recrystallized from methylene chloride petroleum ether to give a shiny yellow solid. An infrared spectrum of this product which shows characteristic peaks for $MoO_2$ at 880 cm$^{-1}$ and 910 cm$^{-1}$ is attached as FIG. 3. The peak attributable to Mo(V) bridged compound at 930–940 cm$^{-1}$ was absent from the infrared spectrum.

EXAMPLE 16

In this example, Dioxobis(dioctyldithiocarbamato)Mo(VI) was prepared as follows: To a mechanically stirred mixture of a solution of 12.2 g (0.05mole) of sodium molybdate dihydrate in 1800 ml of deaerated ice water mixture and 400 ml of chloroform were added simultenaeously through two dropping funnels a solution of 12.2 g of glacial acetic acid in 400 ml of deaerated cold water and a solution of potassium dioctyldithiocarbamate prepared from 24.1 (0.1 mole) of dioctylamine in 400 ml of chloroform. A strong $N_2$ current was passed through the mixture throughout. After allowing to stir for one hour while maintaining the temperature at 0°–5° C., the chloroform solution was separated. The aqueous solution was extracted with chloroform. The combined $CHCl_3$ extracts and solution was backwashed with water (2×300 ml), dried over $MgSO_4$ and filtered.

An infrared spectrum of the chloroform solution evaporated on KBR plates showed strong peaks at 883 cm$^{-1}$, 918 cm$^{-1}$ and 1512 cm$^{-1}$. The peak attributable to Mo(V) at 940 cm$^1$ was absent.

EXAMPLE 17

In this example, Dioxobis(didodecyldithiocarbamato)Mo(VI) was prepared as follows: To a stirred solution of 3 g of sodium molybdate dihydrate in 1.2 l of deaerated ice water mixture was added 250 ml of $CHCl_3$. To the mixture were added simultaneously solutions of potassium didodecyldithiocarbamate (prepared from 7.1 g of didodecylamine, $CS_2$ and KOH) in 250 ml of $CHCl_3$ and a solution of 2.5 ml of glacial acetic acid in 300 ml of deaerated cold water while $N_2$ was bubbled through the mixture. The solutions were added through dropping funnels and rates were adjusted so that the additions were complete in equal time. After allowing to stir for 1.5 hr the mixture was transferred into a separatory funnel and the bottom $CHCl_3$ layer was separated. The top aqueous layer was extracted with $CHCl_3$ (2×100 ml). The extracts and $CHCl_3$ layer were combined, washed with water (2×200 ml), dried over $MgSO_4$ and filtered.

A sample of brownish yellow filtrate was concentrated by blowing $N_2$ and analyzed by infrared spectroscopy. It showed the presence of strong peaks at 882 and 908 cm$^{-1}$ Mo(VI) and a single strong peak at 1504 cm$^{-1}$ (>N$^+$=C), however, the peak at 940 cm$^{-1}$ Mo(VI) was totally absent.

It is thus clear that via this method, new compositions of matter can be obtained such as Dioxobis(diisopropyldithiocarbamato)Mo(VI) (Example 15) and Dioxobis(didodecyldithiocarbamato)Mo(VI) (Example 17) which could not be obtained via methods of the prior art.

While the present invention has been described and illustrated by reference to particular embodiments thereof, it will be appreciated by those of ordinary skill in the art that the same lends itself to variations not necessarily illustrated herein. For this reason, then, reference should be made solely to the appended claims for purposes of determining the true scope of the present invention.

Having thus described and illustrated the invention, what is claimed is:

1. A method for preparing a dihydrocarbyl substituted dithiocarbamate of molybdenum (VI) comprising the steps of:
(a) combining a salt of a dihydrocarbyl substituted dithiocarbamate, each of said dihydrocarbyl substitutions being the same or a different hydrocarbon radical selected from the group consisting $C_1$–$C_{18}$ straight and branched chain aliphatic radicals, $C_5$–$C_8$ cycloalkyl radicals, alkyl substituted cycloalkyl radicals having from 1 to 3 carbon atoms in the alkyl group and from 5 to 7 carbon atoms in the cycloalkyl group, aryl and aklyl aryl radicals having from 1 to 4 carbon atoms in the akly portion thereof and 6 carbon atoms in the aryl portion thereof or both of said dihydrocarbyl substitutions may be a single cyclo or cycloakyl radical having from about 5 to about 10 carbon atoms, said salt being selected from the group consisting of alkali metal salts, ammonium salts and substituted ammonium salts, wherein one or more of the hydrogen atoms of the ammonium ion is replaced with a hydrocarbon radical, selected from the same group as previously recited, an alkali metal molybdate and an organic acid in an inert atmosphere and at a temperature within the range from about $-10°$ C. to about $+25°$ C., the amount of organic acid present being sufficient to provide a pH within the range from about 5.0 to about 8.0; and (b) recovering a dihydrocarbyl substituted dithiocarbamate of molybdenum (VI).

2. The method of claim 1 wherein said suitable reaction media is water.

3. The method of claim 1 wherein said organic acid is introduced as an aqueous solution thereof.

4. The method of claim 1 wherein said salt is an alkali metal salt of dithiocarbamate.

5. The method of claim 4 wherein said alkali metal is sodium.

6. The method of claim 4 wherein said alkali metal is potassium.

7. The method of claim 4 wherein the alkali metal molybdate is sodium molybdate.

8. The method of claim 1 wherein said salt of dithiocarbamate is prepared in a separate step by combining a dihydrocarbyl substituted amine and carbon disulfide in a suitable reaction medium, thoroughly mixing the dihydrocarbyl substituted amine and the carbon disulfide and thereafter adding a hydroxide selected from the group consisting of alkali metal hydroxide, ammonium hydroxide and substituted ammonium hydroxides in an amount sufficient to provide a pH within the range from about 7.5 to about 12.

9. The method of claim 8 wherein said reaction media is water.

10. The method of claim 1 wherein the temperature is within the range from about $-5°$ C. to about $+5°$ C.

11. The method of claim 1 wherein the dihydrocarbyl substituted dithiocarbamate is a dialkyl-substituted dithiocarbamate.

12. The process of claim 1 wherein said organic acid contains a single carboxylic acid group.

13. The process of claim 12 wherein said organic acid is acetic acid.

* * * * *